US012685493B2

(12) United States Patent
McSweeney et al.

(10) Patent No.: US 12,685,493 B2
(45) Date of Patent: Jul. 21, 2026

(54) ALARM MONITORING AND EVALUATION

(71) Applicant: Welch Allyn, Inc., Skaneateles Falls, NY (US)

(72) Inventors: WonKyung McSweeney, Manlius, NY (US); Allen R. Hart, Maryville, TN (US); Alexandre Hernandez Froio, Syracuse, NY (US); Christopher L Long, Chittenango, NY (US); Rebecca Quilty-Koval, Baldwinsville, NY (US)

(73) Assignee: Welch Allyn, Inc., Skaneateles Falls, NY (US)

( * ) Notice: Subject to any disclaimer, the term of this patent is extended or adjusted under 35 U.S.C. 154(b) by 692 days.

(21) Appl. No.: 18/063,193

(22) Filed: Dec. 8, 2022

(65) Prior Publication Data

US 2023/0190208 A1    Jun. 22, 2023

Related U.S. Application Data

(60) Provisional application No. 63/265,719, filed on Dec. 20, 2021.

(51) Int. Cl.
| | |
|---|---|
| *A61B 5/00* | (2006.01) |
| *G06Q 10/0639* | (2023.01) |
| *G16H 40/40* | (2018.01) |

(52) U.S. Cl.
CPC ............ *A61B 5/746* (2013.01); *A61B 5/7435* (2013.01); *G06Q 10/06393* (2013.01); *G16H 40/40* (2018.01)

(58) Field of Classification Search
CPC ......... A61B 5/746; A61B 5/7435; A61B 5/11; G06Q 10/06393; G16H 40/40; G16H 40/20; G16H 40/63
See application file for complete search history.

(56) References Cited

U.S. PATENT DOCUMENTS

| | | | |
|---|---|---|---|
| 8,417,662 | B2 | 4/2013 | Gawlick |
| 8,775,196 | B2 | 7/2014 | Simpson et al. |
| 9,011,352 | B2 | 4/2015 | Ten Kate et al. |
| 9,265,429 | B2 | 2/2016 | St. Pierre et al. |
| 9,649,073 | B2 | 5/2017 | King et al. |
| 9,700,218 | B2 | 7/2017 | Boyer |
| 9,724,006 | B2 | 8/2017 | Dumont et al. |
| 9,767,667 | B2 * | 9/2017 | Sullivan ................ G16H 40/20 |

(Continued)

FOREIGN PATENT DOCUMENTS

| | | |
|---|---|---|
| WO | 2010055205 A1 | 5/2010 |
| WO | 2011116340 A2 | 9/2011 |

*Primary Examiner* — Rex R Holmes
(74) *Attorney, Agent, or Firm* — Merchant & Gould P.C.

(57) ABSTRACT

A device for monitoring a patient displays a nuisance button on a display device, receives clinician feedback from a selection of the nuisance button, and pauses an active alarm in response to the clinician feedback. The device identifies one or more alarm settings responsible for the clinician feedback and adjusts the one or more alarm settings based on the clinician feedback. The device records the clinician feedback in a device usage log for monitoring usage of the nuisance button. The device generates an alarm notification based on the active alarm, and classifies the alarm notification into a first group in which the alarm notification is a push notification or a second group in which the alarm notification is a pull notification.

11 Claims, 13 Drawing Sheets

(56)                    References Cited

U.S. PATENT DOCUMENTS

| | | | |
|---|---|---|---|
| 9,830,801 | B2 | 11/2017 | Rusin et al. |
| 9,883,801 | B2 | 2/2018 | Stump et al. |
| 9,953,542 | B2 | 4/2018 | Mayou et al. |
| 10,248,762 | B2 | 4/2019 | Treacy et al. |
| 10,262,110 | B2 | 4/2019 | Tonna et al. |
| 10,285,612 | B2 | 5/2019 | Gregg et al. |
| 10,311,696 | B2 | 6/2019 | Janssen |
| 10,347,373 | B2 | 7/2019 | Brill et al. |
| 10,366,787 | B2 | 7/2019 | Sampath et al. |
| 10,387,618 | B2 | 8/2019 | Neuhauser et al. |
| 10,504,356 | B2 | 12/2019 | Takano |
| 10,537,290 | B2 | 1/2020 | De Waele et al. |
| 10,555,704 | B2 | 2/2020 | Averina et al. |
| 10,657,787 | B2 | 5/2020 | Baker et al. |
| 10,728,126 | B2 | 7/2020 | Wu et al. |
| 10,737,025 | B2 | 8/2020 | Morris et al. |
| 10,765,379 | B2 | 9/2020 | Perschbacher et al. |
| 10,786,211 | B2 | 9/2020 | Halperin et al. |
| 10,978,191 | B2 | 4/2021 | Collins, Jr. et al. |
| 11,049,250 | B2 | 6/2021 | Nye et al. |
| 11,055,575 | B2 | 7/2021 | Anushiravani et al. |
| 11,058,368 | B2 | 7/2021 | Schuman et al. |
| 2008/0139898 | A1 | 6/2008 | Johnson et al. |
| 2009/0275807 | A1 | 11/2009 | Sitzman et al. |
| 2013/0181827 | A1* | 7/2013 | Zheng ............... G05B 23/0262 |
| | | | 340/501 |
| 2015/0213205 | A1 | 7/2015 | Van De Sluis et al. |
| 2015/0351695 | A1 | 12/2015 | Cronin |
| 2017/0031449 | A1 | 2/2017 | Karsten et al. |
| 2018/0039740 | A1 | 2/2018 | Frick |
| 2018/0366211 | A1 | 12/2018 | Yang et al. |
| 2019/0150837 | A1 | 5/2019 | Dibia |
| 2020/0113435 | A1 | 4/2020 | Muhsin |

* cited by examiner

400

402
Display Nuisance Button

404
Receive Feedback

406
Determine Attribution of Feedback

408
Adjust Alarm Setting

136

168

6:40

Thursday, November 30

172a

Alert! Severe Alarm Condition, Rm
302, EWS indicating high risk, 9:55am.

172b

Moderate Alarm Condition, Rm 304,
Elevated blood pressure, 10:12am

1000

1002

Receive Alarm Notification

1004

First Classification                    Second Classification

Classify Alarm Notification

1008

Aggregate Alarm Notification

1006

Push Alarm Notification          Yes          1010

Predefined Condition Satisfied?

No          1012

Pull Alarm Notification

ALARM MONITORING AND EVALUATION

BACKGROUND

Alarm fatigue is sensory overload when clinicians are exposed to an excessive number of alarms, which can result in desensitization to alarms. An excessive number of alarms received within a short period of time is sometimes referred to as alarm flooding. Alarm fatigue can result in clinicians ignoring or failing to respond appropriately to such alarms.

Nuisance alarms due to inappropriate alarm settings can contribute to alarm fatigue. Often clinicians are unable to adjust alarm settings due to limited information. Additionally, different care environments can have different workflows for different patient populations making it challenging to address alarm fatigue across multiple care environments.

SUMMARY

In general terms, the present disclosure relates to active alarm communications that reduce alarm fatigue in alarm flooding situations. In one possible configuration, clinician responses to active alarms are monitored and evaluated over time to recommend alarm setting adjustments and/or changes to alarm algorithms to reduce alarm fatigue. Various aspects are described in this disclosure, which include, but are not limited to, the following aspects.

In one aspect, a device for monitoring a patient comprises: a display device; at least one processing device; and a memory device storing instructions which, when executed by the at least one processing device, cause the device to: display a nuisance button on the display device; receive clinician feedback from a selection of the nuisance button; pause an active alarm in response to the clinician feedback; identify one or more alarm settings responsible for the clinician feedback; and adjust the one or more alarm settings based on the clinician feedback.

In another aspect, a device for monitoring a patient comprises: at least one processing device; and a memory device storing instructions which, when executed by the at least one processing device, cause the device to: detect an event on the device, wherein the event includes a clinician input that an active alarm is a nuisance; generate a device usage log based on the event; aggregate a plurality of device usage logs over a period of time; determine key performance indicators based on the plurality of device usage logs; and recommend an optimal setting for one or more alarms based on the key performance indicators.

Another aspect relates to a device comprising: at least one processing device; and a memory device storing instructions which, when executed by the at least one processing device, cause the device to: receive a notification that an active alarm is triggered; classify the notification into at least one of: a first group which pushes the notification to a mobile device; and a second group which aggregates the active alarm with additional active alarms, and allows the notification to be pulled by the mobile device; determine whether a predefined condition is satisfied by the active alarm when aggregated with the additional active alarms in the second group; and when the predefined condition is satisfied, push the notification when classified in the second group to the mobile device.

Another aspect relates to a method of monitoring a patient, comprising: displaying a nuisance button; receiving clinician feedback from a selection of the nuisance button; pausing an active alarm in response to the clinician feedback; identifying one or more alarm settings responsible for the clinician feedback; and adjusting the one or more alarm settings based on the clinician feedback.

Another aspect relates to a method of monitoring a patient, comprising: detecting an event on a device monitoring the patient, wherein the event includes a clinician input that an active alarm is a nuisance; generating a device usage log based on the event; aggregating a plurality of device usage logs over a period of time; determining key performance indicators based on the plurality of device usage logs; and recommending an optimal setting for one or more alarms based on the key performance indicators.

DESCRIPTION OF THE FIGURES

The following drawing figures, which form a part of this application, are illustrative of the described technology and are not meant to limit the scope of the disclosure in any manner.

DETAILED DESCRIPTION

Figure 1:
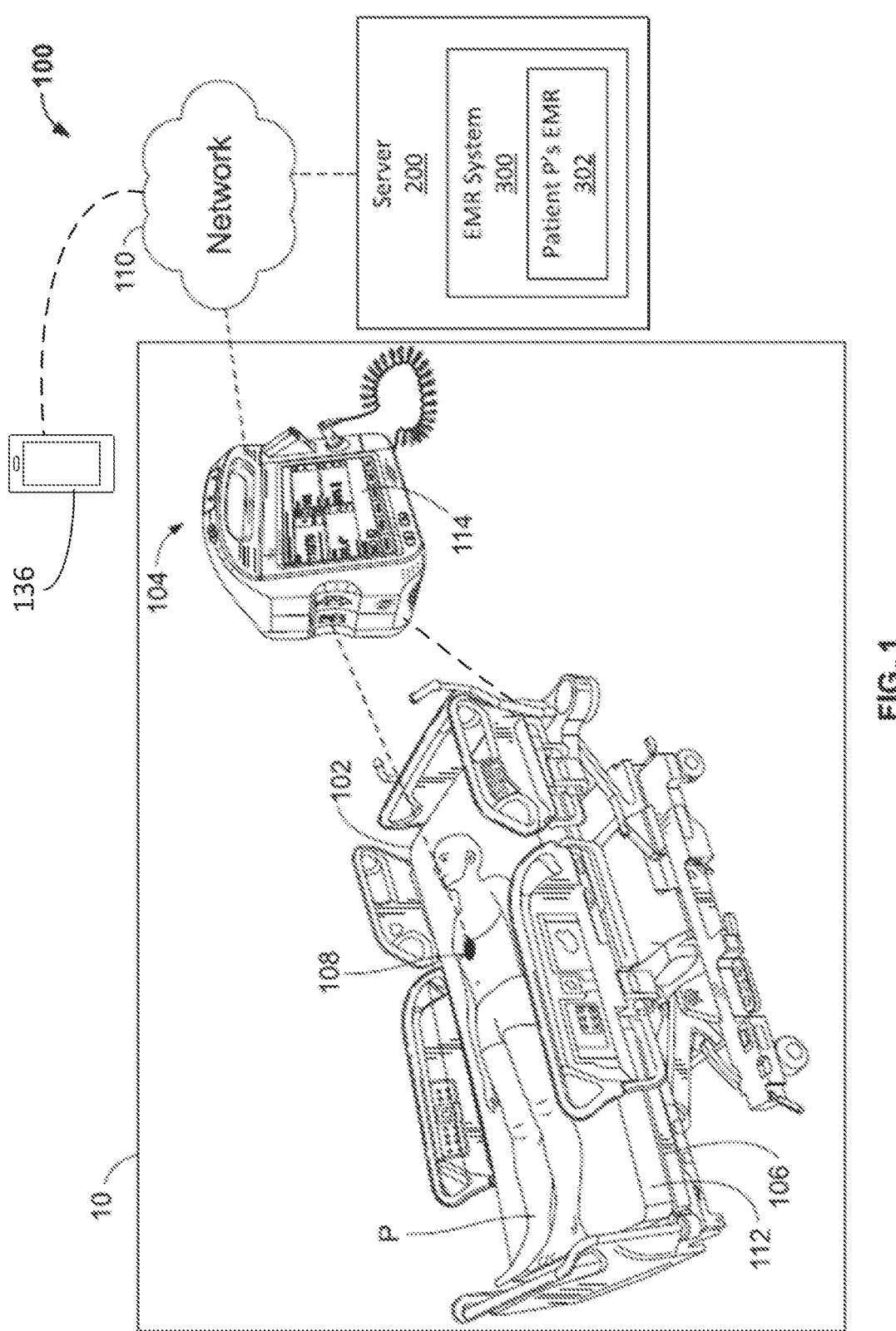
FIG. 1 illustrates an example of a system including a monitor device for monitoring physiological variables of a patient resting on a patient support system.

FIG. 1 illustrates an example of a system 100 for monitoring physiological variables of a patient P who is shown resting on a patient support system 102. The system 100 includes the patient support system 102, as well as a monitor device 104, a motion sensor 106, and one or more physiological sensors 108, which are all shown inside an area 10. In some examples, the area 10 is a patient room, a mid-acuity or low-acuity environment, a pre-operative or postoperative holding area, an operating room, a waiting room, or other type of area within a healthcare facility such as a hospital, a surgical center, a nursing home, a long term care facility, or similar type of facility. In further examples, the area 10 can be the patient P's home.

The patient P is a person, such as a patient, who is being clinically treated by one or more clinicians in the area 10. Examples of clinicians include primary care providers (e.g., doctors, nurse practitioners, and physician assistants), nursing care providers (e.g., nurses), specialty care providers (e.g., professionals in various specialties), and health professionals that provide preventive, curative, promotional and rehabilitative health care services.

In the example shown in FIG. 1, the patient support system 102 is a hospital bed. In other examples, the patient support system 102 is another type of bed, lift, chair, wheelchair, stretcher, surgical table, and the like, which can support the patient P in the area 10.

As shown in FIG. 1, the patient support system 102 is communicatively connected to the monitor device 104 through a wireless or wired link. The patient support system 102 includes a frame that supports a mattress 112, and siderails that are coupled to the frame.

The monitor device 104 is an example of an integrator device that receives data from source devices such as the patient support system 102, the motion sensor 106, and the one or more physiological sensors 108. The monitor device 104 includes a computing device 120 (shown in FIG. 2) that processes the data from the source devices to make decisions such as whether to delay, suppress, or trigger one or more alarms. The monitor device 104 includes a display device 114 for displaying the data acquired from the source devices including the patient support system 102, the motion sensor 106, and the one or more physiological sensors 108.

The monitor device 104 may be any suitable type of monitoring device. In the example provided in FIG. 1, the monitor device 104 is illustrated as a multi-parameter device which displays on the display device 114 multiple parameters detected from the source devices. In alternative examples, the monitor device 104 can be a single-parameter device.

The monitor device 104 can accommodate various alarm features for monitored physiological variables such as traditional alarm thresholds (e.g., upper and lower alarm limits), traditional alarm delays, weighted alarm delays, multivariate index alarms, and the like. In certain examples, the monitor device 104 is a spot monitor, and may include the features described in U.S. Pat. No. 9,265,429, which is herein incorporated by reference in its entirety.

The system 100 can include a plurality of the physiological sensors 108 for monitoring multiple physiological variables. In some examples, a physiological sensor 108 is a multiparameter sensor that can measure multiple physiological variables as a single device.

Examples of the one or more physiological sensors 108 include an electrocardiogram (ECG) sensor, a pulse oximeter sensor that measures blood oxygen saturation (SpO2), a blood pressure sensor for measuring both systolic and diastolic blood pressure, a heart rate sensor, a respiration rate sensor, an end tidal carbon dioxide (etCO2) sensor that can also be used to measure integrated pulmonary index (IPI), and the like. The one or more physiological sensors 108 can also combine two or more sensors into a single sensor device.

As shown in FIG. 1, the monitor device 104 communicates with a server 200 via a communications network 110. The server 200 operates to manage the patient P's medical history and information. The server 200 can be operated by a healthcare service provider, such as a hospital or medical clinic. The monitor device 104 sends physiological data acquired from the source devices to the server 200 via the connection to the communications network 110. In at least some examples, the server 200 is a cloud server or similar type of server.

The server 200 can include an electronic medical record (EMR) system 300 (alternatively termed electronic health record (EHR)). Advantageously, the server 200 can automatically store the physiological data acquired from the monitor device 104 in an electronic medical record 302 or electronic health record of the patient P located in the EMR system 300 via the connection with the monitor device 104 over the communications network 110.

In the example shown in FIG. 1, the motion sensor 106 is a motion sensor positioned below, within, or on top of a mattress 112 of the patient support system 102. The motion sensor 106 can include piezoelectric sensors, load cells, or combinations thereof that detect movements of the patient P while the patient P is supported on the patient support system 102.

In some examples, the motion sensor 106 may be an accelerometer attached to the patient P, or incorporated into a physiological sensor 108 and/or into one or more other sensing devices that are attached to the patient P. In such examples, physiological sensing and motion detection functions are combined in one device. Multiple such devices may be used on the patient P. For example, a combined ECG/motion detection device and/or a combined respiration rate/motion detection device may be used on the patient P at the same time.

The motion sensor 106 detects motion by the patient P, which can affect or influence the heart rate, blood pressure, and respiration rate data sensed by the one or more physiological sensors 108. The motion sensor 106 senses motion by the patient P (e.g., by using piezoelectric or load cell sensors positioned below, within, or on top of a mattress 112 or accelerometers attached to the patient P), and transmits the sensed motion data to the monitor device 104 while the one or more physiological sensors 108 sense physiological data such as the heart rate, blood pressure, or respiration rate, and transmit the physiological data to the monitor device 104.

The communications network 110 communicates data between one or more devices, such as between the monitor device 104, the server 200, and a mobile device 136 that is utilized by a clinician when caring for patients within the healthcare facility. Examples of the mobile device 136 can include a smartphone, a tablet computer, and other portable computing devices. In some examples, the communications network 110 is also used to communicate data between one or more devices inside the area 10 such as between the patient support system 102, the monitor device 104, the motion sensor 106, the physiological sensors 108, and other devices.

The communications network 110 can include any type of wired or wireless connections or any combinations thereof. Examples of wireless connections include cellular network connections such as 4G or 5G. Wireless connections can also be accomplished using Wi-Fi, ultra-wideband (UWB), Bluetooth, and similar types of wireless connections.

Figure 2:
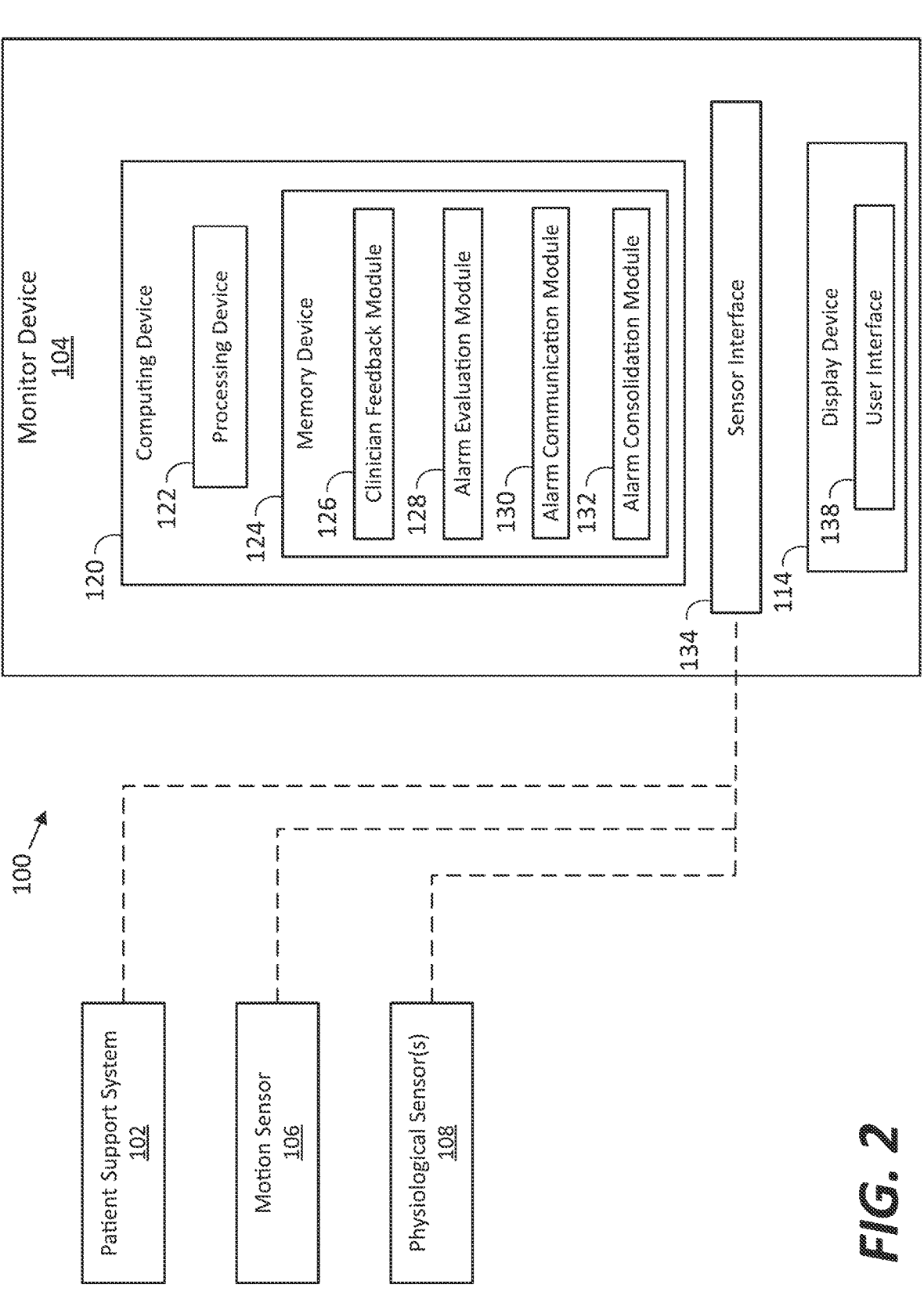
FIG. 2 schematically illustrates an example of the system of FIG. 1, which includes various source devices connected to the monitor device.

FIG. 2 schematically illustrates an example of the system 100. As shown in FIG. 2, the monitor device 104 includes a computing device 120 having a processing device 122 and a memory device 124. The processing device 122 is an example of a processing unit such as a central processing unit (CPU). The processing device 122 can include one or more central processing units (CPU). In some examples, the processing device 122 can include one or more digital signal processors, field-programmable gate arrays, or other electronic circuits.

The memory device 124 operates to store data and instructions for execution by the processing device 122, including a clinician feedback module 126, an alarm evaluation module 128, an alarm communication module 130, and an alarm consolidation module 132. Each of these modules will be described in more detail below. The memory device 124 includes computer-readable media, which may include any media that can be accessed by the monitor device 104. By way of illustrative example, computer-readable media include computer readable storage media and computer readable communication media.

Computer readable storage media includes volatile and nonvolatile, removable and non-removable media implemented in any device configured to store information such as computer readable instructions, data structures, program modules, or other data. Computer readable storage media can include, but is not limited to, random access memory, read only memory, electrically erasable programmable read only memory, flash memory, and other memory technology, including any medium that can be used to store information that can be accessed by the monitor device 104. The computer readable storage media is non-transitory.

Computer readable communication media embodies computer readable instructions, data structures, program modules or other data in a modulated data signal such as a carrier wave or other transport mechanism and includes any information delivery media. The term "modulated data signal" refers to a signal that has one or more of its characteristics set or changed in such a manner as to encode information in the signal. By way of example, computer readable communication media includes wired media such as a wired network or direct-wired connection, and wireless media such as acoustic, radio frequency, infrared, and other wireless media. Combinations of any of the above are within the scope of computer readable media.

The monitor device 104 further includes a sensor interface 134 that operates to communicate with the various source devices of the system 100 such as the patient support system 102, the motion sensor 106, and the one or more physiological sensors 108. Additional examples of source devices can include infusion pumps, ventilators, and the like.

The sensor interface 134 can include both wired interfaces and wireless interfaces. For example, the source devices can wirelessly connect to the sensor interface 134 through Wi-Fi, ultra-wideband (UWB), Bluetooth, and similar types of wireless connections. In further examples, the source devices can connect to the monitor device 104 using wired connections that can plug into one or more sockets or receptacles of the sensor interface 134.

As shown in FIG. 2, the monitor device 104 includes the display device 114, which operates to display a user interface 138. In some examples, the display device 114 is a touchscreen such that the user interface 138 operates to receive inputs from a clinician. In such examples, the display device 114 operates as both a display device and a user input device. The monitor device 104 can also support physical buttons on a housing of the device that operate to receive inputs from the clinician to control operation of the monitor device and enter data.

Figure 3:
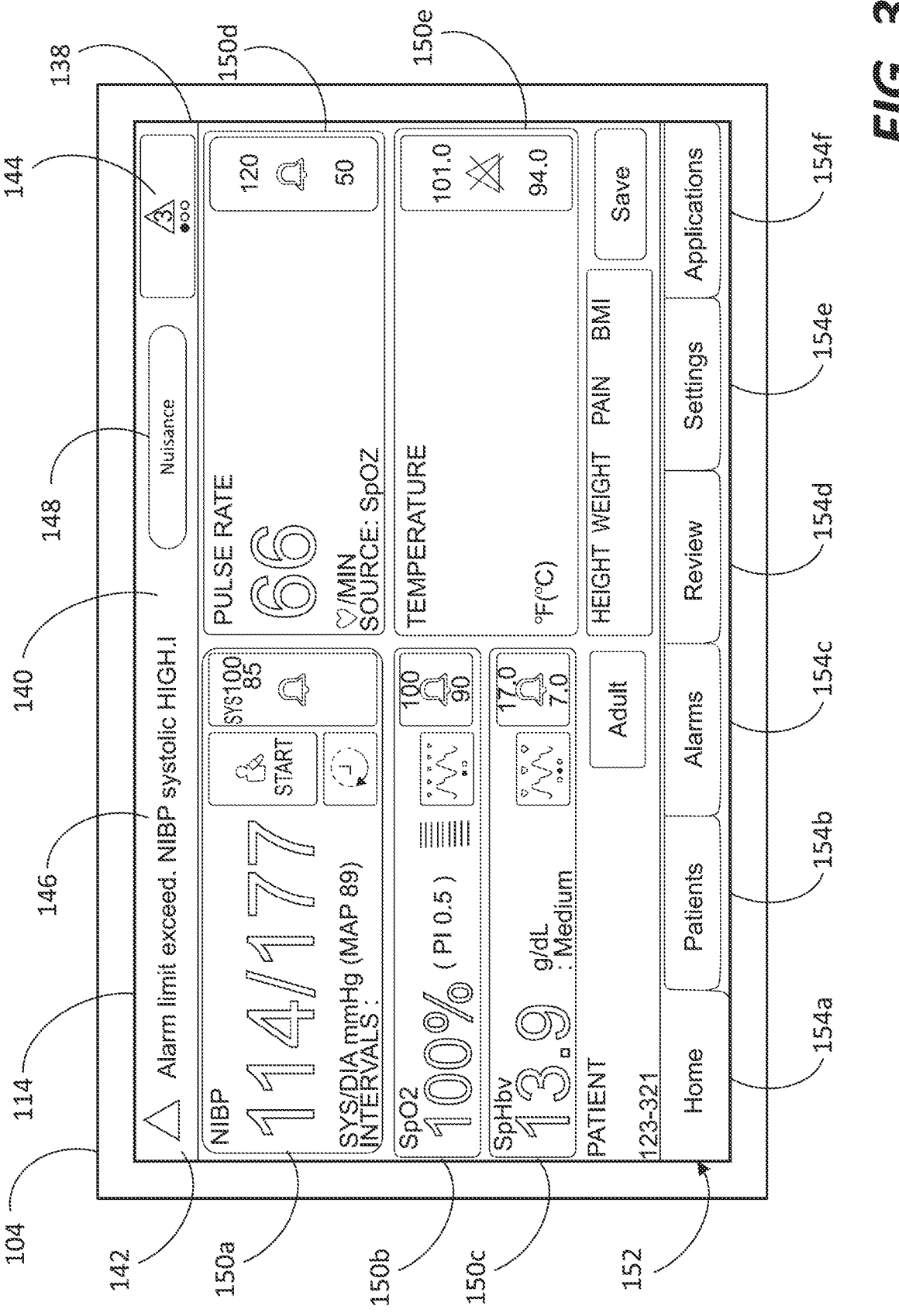
FIG. 3 shows an example of a nuisance button included on a user interface of the monitor device of FIG. 1.

FIG. 3 shows an example of a nuisance button 148 included in a user interface 138 displayed on the display device 114 of the monitor device 104. The nuisance button 148 receives clinician feedback on an active alarm such as a clinician input that the active alarm is a nuisance. In certain examples, display of the nuisance button 148 and the clinician feedback received from the nuisance button 148 is controlled and monitored by the clinician feedback module 126.

In the illustrative example provided in FIG. 3, the nuisance button 148 is displayed in a device status area 140. In this example, the device status area 140 displays a message 146 regarding a status of the patient being monitored by the monitor device 104. For example, the message 146 can indicate an alarm is triggered. In some further examples, the message 146 can also provide a reason for why the alarm is triggered. In the illustrative example provided in FIG. 3, the message 146 states "Alarm limit exceeded. NIBP systolic HIGH."

In the example shown in FIG. 3, the device status area 140 is displayed in a top portion of the user interface 138. In alternative examples, the device status area 140 can be displayed elsewhere on the user interface 138 such as on a bottom portion or elsewhere.

The device status area 140 includes an alarm pause input 142 that can be selected by a clinician to turn off or pause an alarm for a predetermined interval. When the alarm pause input 142 is selected to pause an alarm, a visual indication of the triggered alarm will remain in the device status area 140 until the condition is corrected or another measurement is taken. In some examples, when the alarm pause input 142 is selected to pause an alarm, a timer can display a countdown for an alarm audio tone and/or flashing light to return after completion of the predetermined interval. The alarm pause input 142 can be selected again to restart the timer to pause the alarm audio tone and/or flashing light for the predetermined interval.

The device status area 140 further includes an alarm toggle input 144 that can be selected by a clinician to toggle between multiple alarms in the device status area 140 when multiple alarms are triggered. Thus, the clinician can use the alarm pause input 142 and the alarm toggle input 144 to turn off or pause multiple alarms in the device status area 140.

The nuisance button 148 provides a direct clinician feedback channel on the monitor device 104 for nuisance alarms. In certain examples, a nuisance alarm occurs when there is no actionable clinical intervention that can be done to stop the alarm from being triggered. In some instances, a nuisance alarm may be due to inappropriate alarm settings.

The nuisance button 148 when selected by a clinician also acts as an alarm input that when received by the monitor device 104, causes the monitor devise to pause or adjust one or more thresholds of the triggered alarm. Thus, the nuisance button 148 is a selectable input on the user interface 138 that functions as both a direct clinician feedback channel and an alarm input that does not add extra burden to the workflow of the monitor device 104.

Additionally, the nuisance button 148 is provided on the user interface 138 in addition to the alarm pause input 142. The nuisance button 148 is used by the monitor device 104 to differentiate between situations when a clinician performs an intervention to correct a condition that is triggering an alarm (in which case the clinician can select the alarm pause input 142) from situations when the clinician pauses the alarm because it is a nuisance (in which case the clinician can select the nuisance button 148). Thus, the nuisance button 148 when selected provides additional information that is not received from the alarm pause input 142.

In addition to the device status area 140, the user interface 138 further includes display modules 150a-150e for various physiological variables of the patient P that are being monitored by the monitor device 104. For example, the user interface 138 includes a display module 150a for displaying a non-invasive blood pressure (NIBP) measurement of the patient P (including both systolic and diastolic blood pressure measurements), a display module 150b for displaying a blood oxygen saturation (SpO2) measurement of the patient P, a display module 150c for displaying a continuous total hemoglobin (SpHb) measurement of the patient P, a display module 150d for displaying a pulse rate measurement of the patient P, and a display module 150e for displaying a temperature measurement of the patient P. In other examples, the user interface 138 can display fewer display modules for displaying fewer physiological variables of the patient P that are being monitored by the monitor device 104. Also, the user interface 138 can display additional display modules for displaying additional types of physiological variables of the patient P that are being monitored by the monitor device 104.

The user interface 138 further includes a display ribbon 152 that includes a plurality of tabs 154a-154f that are selectable by a clinician to display various screens and information on the monitor device 104. In the example shown in FIG. 3, a home tab 154a is selected for displaying a home screen on the display device 114 that includes the display modules 150a-150e for the various physiological variables of the patient P that are being monitored by the monitor device 104. The display ribbon 152 further includes a patients tab 154b, an alarms tab 154c, a review tab 154d, a settings tab 154e, and an applications tab 154f that can each be selected by the clinician to view additional screens and information on the monitor device 104.

Figure 4:
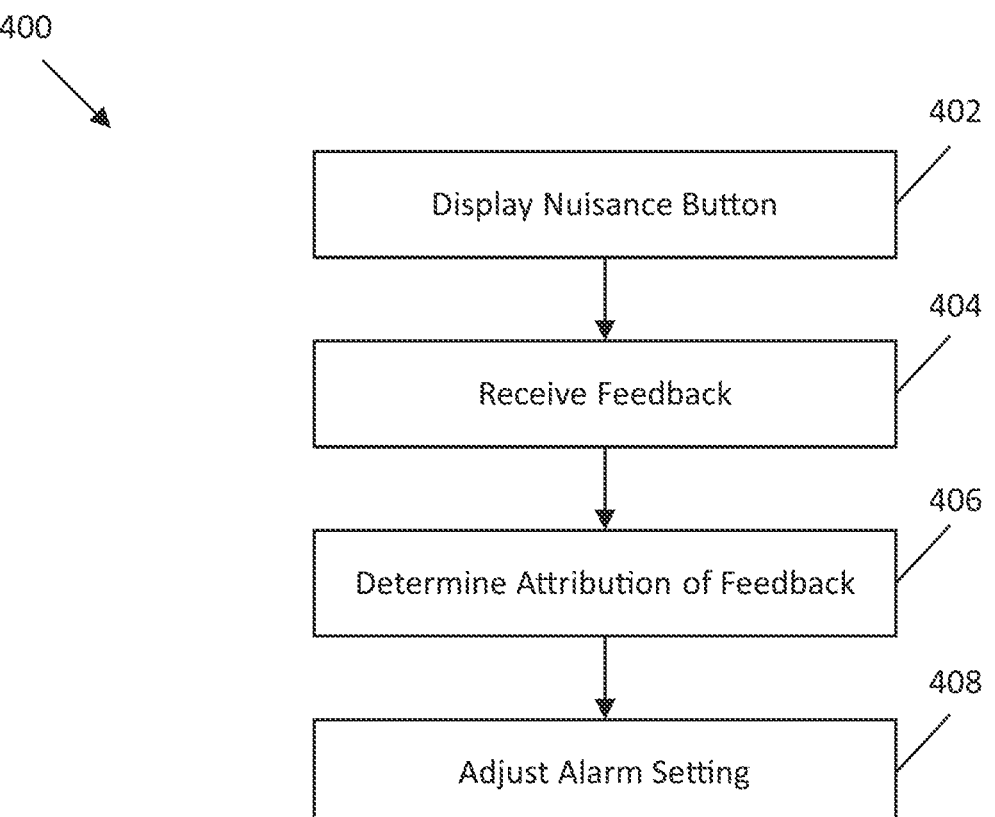
FIG. 4 schematically illustrates an example of a method of adjusting one or more alarm settings based on clinician feedback received from the nuisance button of FIG. 3.

FIG. 4 schematically illustrates an example of a method 400 of adjusting one or more alarm settings based on clinician feedback received from the nuisance button 148. As described above, the nuisance button 148 provides an efficient and easy to use feedback channel for a clinician to indicate a false alarm, and the monitor device 104 can use this feedback to adjust alarm settings to reduce a likelihood of future false alarms. In certain examples, the method 400 is performed by the clinician feedback module 126 installed on the monitor device 104.

As shown in FIG. 4, the method 400 includes an operation 402 of displaying the nuisance button 148 such as on the user interface 138 displayed on the display device 114 shown in FIG. 3. The method 400 further includes an operation 404 of receiving feedback via a selection of the nuisance button 148 by a clinician. As described above, the display device 114 is a touchscreen such that the user interface 138 operates to receive the selection of the nuisance button 148 from a clinician touching the nuisance button 148 with their finger, with a stylus, or other similar devices. Alternatively, the selection of the nuisance button 148 can be received by a clinician pressing a physical button on the housing of the monitor device 104.

Next, the method 400 includes an operation 406 of determining an attribution of the feedback received from operation 404. For example, operation 406 can include identifying one or more alarm settings that are responsible for a false alarm based on the feedback received from selection of the nuisance button 148. For example, operation 406 can include determining that an algorithm for a non-invasive blood pressure (NIBP) alarm is responsible for a false alarm. Additionally, operation 406 can include identifying one or more patient conditions that are responsible for the false alarm such as patient motion detected by the motion sensor 106.

Next, the method 400 includes an operation 408 of adjusting one or more alarm settings based on the attribution of the feedback determined from operation 406. In one example, the one or more alarm settings can be adjusted such as to increase an upper alarm limit, or decrease a lower alarm limit to reduce the likelihood of a false alarm. For example, rebasing can be performed where measurement readings around when the nuisance button 148 was pressed by the clinician will be collected to provide a new baseline or new alarm thresholds.

As another example, the one or more alarm settings can be adjusted to filter or otherwise ignore data when one or more conditions are detected, such as movement by the patient P detected by the motion sensor 106. As a further example, when patient motion is detected around when the nuisance button 148 was pressed by the clinician, this information can be used to increase a motion weighted delay for the alarm.

In one embodiment, operation 408 includes dynamically updating the one or more alarm settings in real time or in near real-time. For example, the one or more alarm settings can be updated while the monitor device 104 is being used to monitor the physiological variables of the patient P. In such embodiment, operation 408 can include using machine learning and/or statistical modeling to dynamically update the one or more alarm settings in real time or in near real-time. Advantageously, this can provide an immediate reduction of false alarms based on the feedback received from the nuisance button 148 during operation of the monitor device 104.

In some examples, operation 408 can include updating the one or more alarm settings based on a learning rate that is adjustable by a clinician. The learning rate determines how fast the monitor device 104 adjusts the one or more alarm settings based on the feedback received from the nuisance button 148. For example, increasing a speed of the learning rate can make the method 400 more sensitive. Alternatively, decreasing the speed of the learning rate can make the method 400 less sensitive. As an illustrative example, the learning rate can be selected to adjust the one or more alarm settings in real-time or in near real-time, or can be selected to adjust the one or more alarm settings every half hour, every hour, every six hours, and the like. In another example, the learning rate can be based on a threshold number of clicks of the nuisance button 148 that must be satisfied before an alarm setting is adjusted. In certain examples, the learning rate can be adjusted by selecting the settings tab 154e to display a settings screen that includes a plurality of settings that are adjustable by the clinician, which can include the learning rate.

In some examples, operation 408 includes automatically adjusting the one or more alarm settings based on the feedback from the nuisance button 148 without requiring input from the clinician. In alternative examples, operation 408 includes prompting the clinician to accept one or more recommended alarm settings based on the feedback received from the nuisance button 148, such that the one or more alarm settings are not automatically adjusted. Instead, the clinician must accept the recommended settings. Otherwise, when the clinician declines the recommended alarm settings, the one or more alarm settings are not adjusted.

In an alternative embodiment, the feedback from the nuisance button 148, the alarm settings at the time of the feedback from the nuisance button 148, and the physiological variables of the patient P measured at the time of the feedback from the nuisance button 148, are collected over a period of time, and operation 408 can include updating the one or more alarm settings when the monitor device 104 is offline (i.e., not being used to monitor the patient P).

The data is collected on the feedback from the nuisance button 148, the alarm settings at the time of the feedback from the nuisance button 148, and the physiological variables of the patient P measured at the time of the feedback from the nuisance button 148 can be stored on the memory device 124 of the monitor device 104. Alternatively, this data can be stored on the server 200 or elsewhere, and can be accessed by the monitor device 104 and/or other devices.

The data is collected on the feedback from the nuisance button 148, the alarm settings at the time of the feedback from the nuisance button 148, and the physiological variables P measured at the time of the feedback from the nuisance button 148 can be combined from multiple monitor devices in the healthcare facility, and alarm settings of the monitor devices 104 in the healthcare facility can be updated in batches. In some examples, one or more alarm settings are updated in batches for monitor devices 104 that are being used to monitor patients of the same cohort (e.g., pediatric), and/or for monitor devices 104 that are being used in the same department or unit within the healthcare facility, such as a neonatal intensive care unit (ICU).

In some examples, transfer learning is used to update the alarm settings for multiple monitor devices based on the feedback received from the nuisance button 148. For example, transfer learning, which is subset of machine learning, can be used to store knowledge gained while adjusting the alarm settings on one of the monitor devices 104, to adjust the alarm settings on other monitor devices 30 that are being used to monitor patients of the same cohort, and/or that are being used in the same department or unit within the healthcare facility.

Figure 5:
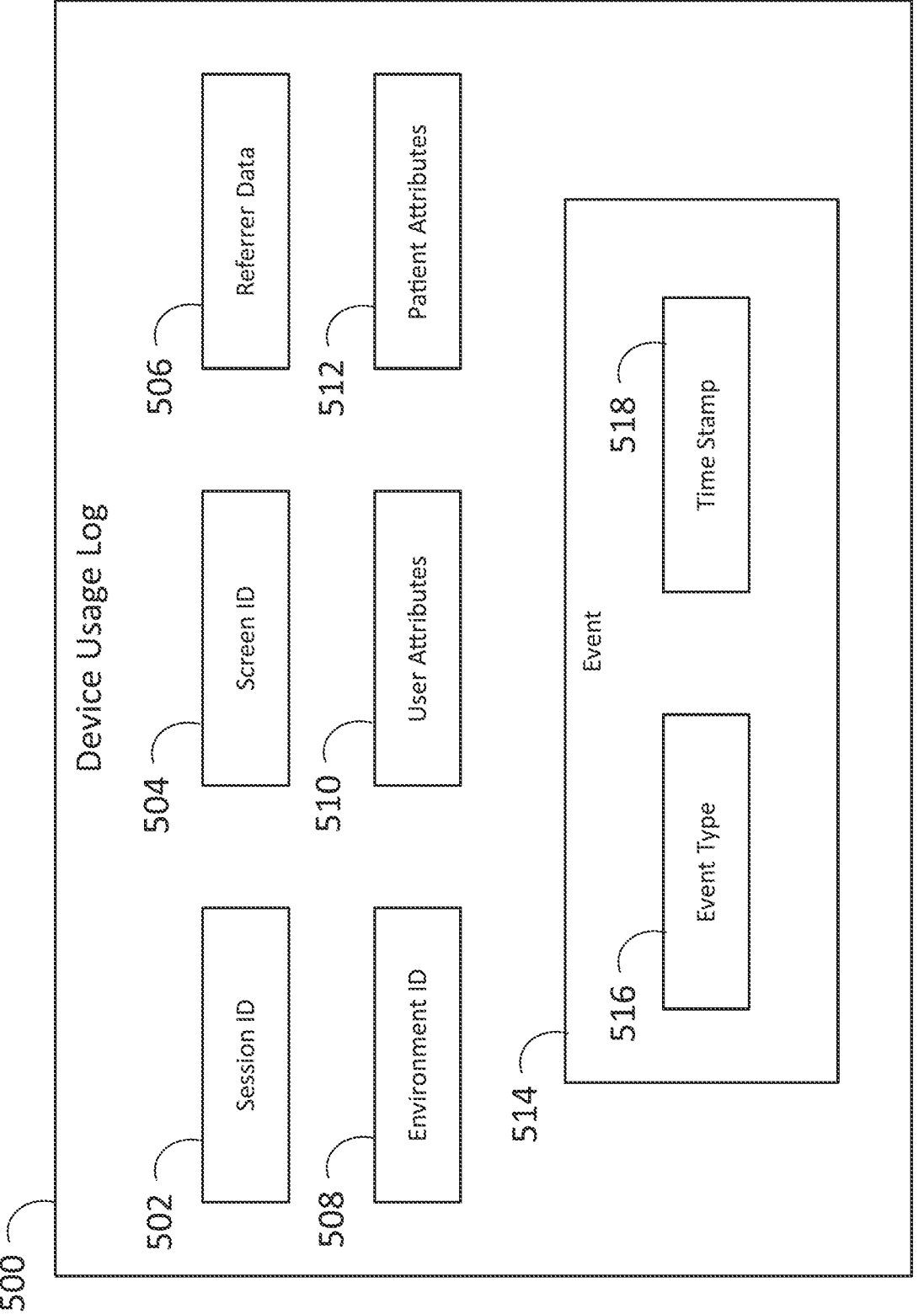
FIG. 5 illustrates an example of a device usage log that can be used to evaluate one or more alarm features of the monitor device of FIG. 1.

FIG. 5 illustrates an example of a device usage log 500 that can be used to monitor and evaluate one or more alarm features of the monitor device 104. For example, the device usage log 500 can be used to monitor and evaluate usage of the nuisance button 148.

The device usage log 500 is an example of a clickstream data schema or data set. In some examples, the device usage log 500 is generated in JavaScript Object Notation (JSON) format, or in a similar type of data format. The device usage log 500 is generated each time an event 514 on the monitor device 104 is detected, which will be described in more detail below.

The device usage log 500 is used to attribute user interactions with the alarm features of the monitor device 104 in various environments and under various conditions. As will be described in more detail, the device usage log 500 can be used to generate recommendations for updating and improving the one or more alarm features based on the user interactions.

For example the device usage log 500 can be used to attribute positive user interactions, negative user interactions, and neutral user interactions to the alarm features. Positive user interactions are user interactions that follow an expected or intended path, negative user interactions are user interactions that do not follow an expected or intended path, and neutral user interactions are user interactions that are partially positive or partially negative.

In some examples, the device usage log 500 is limited to device usage information (e.g., user interactions) without patient data and monitored physiological variables. This can increase the extensibility of the device usage log 500 across various platforms and devices.

Alternatively, the device usage log 500 can include patient data including monitored physiological variables. In such examples, the patient data and monitored physiological variables can be mapped to the device usage information. This can allow use of the device usage log 500 for recommending alarm setting adjustments and/or building new alarm algorithms.

As shown in FIG. 5, the device usage log 500 includes a session ID 502 which defines a scope of attribution. The session ID 502 can provide more efficient downstream data processing. For example, each session for the monitor devices 104 can be processed in parallel into key performance indicators (KPIs), which can then be aggregated. The scope of attribution can include a time cutoff (e.g., new session starts after a predetermined time interval), or a patient cutoff (e.g., new session starts when the monitor device 104 is used on a new patient).

The device usage log 500 further includes a screen ID 504 which identifies a screen displayed on the display device 114 for evaluation. The screen ID 504 can include any type of general screen or page that is displayed on the display device 114. The screen ID 504 can also include a list of screens when a screen has a tile-style display of multiple features.

As an illustrative example, the screen ID 504 can include any of the screens identified on the display ribbon 152 (see FIG. 2) such as a home screen (displayed when the clinician selects the home tab 154*a*), a patients screen (displayed when the clinician selects the patients tab 154*b*), an alarms screen (displayed when the clinician selects the alarms tab 154*c*), a review screen (displayed when the clinician selects the review tab 154*d*), a settings screen (displayed when the clinician selects the settings tab 154*e*), an applications screen (displayed when the clinician selects the applications tab 154*f*), and any other additional screens that can be displayed on the display device 114 in response to user interactions on the monitor device 104.

The device usage log 500 further includes referrer data 506 which indicates how a user such as a clinician landed on the screen identified by the screen ID 504. For example, when there are multiple ways to get to a screen (e.g., alarms screen), the referrer data 506 can identify how the user arrived to the screen (e.g., by clicking a link on a previous screen).

The device usage log 500 further includes an environment ID 508 that identifies an environment in which the monitor device 104 is deployed such as a healthcare facility, or a unit, a department, or a location within the healthcare facility. Additionally, the environment ID 508 can identify a platform on which the screen identified by the screen ID 504 is accessed such as a spot monitor platform when the screen is access on the monitor device 104, a mobile platform when the screen is accessed on the mobile device 136, and/or whether the screen is remotely accessed (such as through a mobile device 136 or a central nurse station).

The device usage log 500 can include user attributes 510 that identify attributes of the user who accessed the screen identified by the screen ID 504 such as their position or title (e.g., medical doctor, nurse, or physician assistant), their credentials, and/or their assigned unit or department within the healthcare facility. The user attributes can obfuscate information that can identify the user such as the user's badge ID, name, and the like.

In some examples, the device usage log 500 can include patient attributes 512 that can identify attributes of the patient such as their age, gender, diagnoses, treatments, medications, and/or unit or department within the healthcare facility where they are admitted. The patient attributes 512 can obfuscate information that can be used to identify the patient such as the patient's medical record number, name, and the like.

The device usage log 500 further includes an event 514 which comprises an event type 516 and a time stamp 518 indicating when the event occurred. Illustrative examples of event types 516 include, without limitation, alarm triggered, alarm paused, alarm reset, alarm adjusted (e.g., upper alarm limit increased, lower alarm limit decreased, etc.), alarm settings viewed, physiological variable trends viewed (e.g., zoom in and out of trends, adjust start time for trend, adjust end time for trend, etc.), patient information viewed, nuisance button 148 selected, and the like. The device usage log 500 can be generated each time an event type 516 is detected.

The device usage logs 500 are collected and aggregated to monitor key performance indicators (KPIs). Illustrative examples of KPIs that can be monitored from the device usage logs 500 are provided in Table 1. These KPIs are provided by way of illustrative example and are not exhaustive such that additional types of KPIs can be monitored from the device usage logs 500.

TABLE 1

| Key Performance Indicator (KPI) |
| --- |
| 1. Number of alarm setting changes from default by hospital unit type. |
| 2. Number of alarms triggered per different alarm settings by hospital unit type. |
| 3. Number of buttons clicked by clinician from alarm being triggered to alarm reset (or patient stabilization). |
| 4. Time from alarm being triggered to alarm reset (or patient stabilization). |
| 5. Clinician interaction time when alarm setting is changed. |
| 6. Frequently viewed information before alarm setting is changed. |
| 7. Click through rate of visualization features. |
| 8. Lingering time of visualization features. |
| 9. Departure rate of recommended alarm setting adjustment or alarm feature (e.g., alarm feature recommended to user and user clicked something else). |
| 10. Alarm feature usage (e.g. motion weighted alarm delay usage). |
| 11. Success rate of alarm features (e.g. motion weighted alarm delay eventually alarmed). |
| 12. Alarm feature KPI variance by unit. |
| 13. Alarm feature KPI variance by patient inter/intra unit. |

The KPIs can be used to monitor and evaluate the alarm features of the monitor device 104 across different care environments that can have different workflows for different patient populations. The KPIs can be used to mitigate alarm fatigue by identifying optimal alarm setting recommendations based on department or unit within the healthcare facility and/or patient population to reduce the number of alarms triggered and/or to reduce user interaction times. Also, when combined with patient data and monitored physiological variables, the KPIs can be used to build new alarm algorithms to reduce the likelihood of nuisance alarms.

Figure 6:
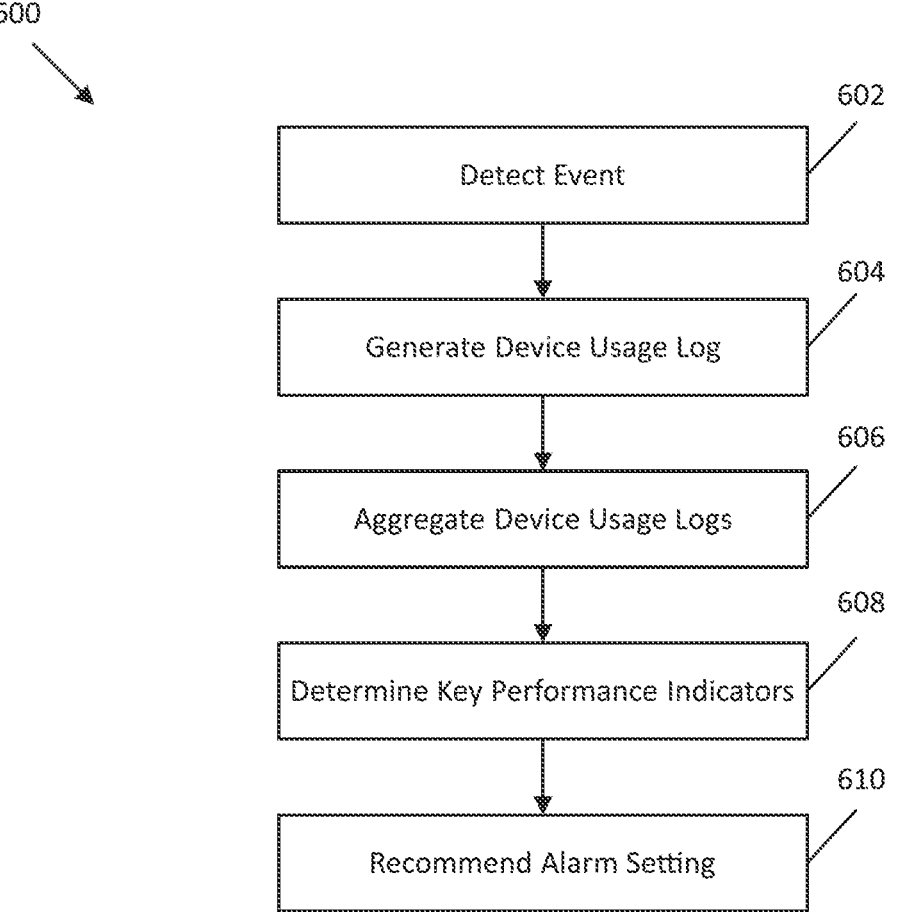
FIG. 6 schematically illustrates an example of a method of using the device usage log of FIG. 5 to monitor and evaluate alarm features of the monitor device of FIG. 1.

FIG. 6 schematically illustrates an example of a method 600 of monitoring and evaluating alarm features of the monitor device 104. In certain examples, the method 600 is performed by the alarm evaluation module 128 installed on the monitor device 104.

As shown in FIG. 6, the method 600 includes an operation 602 of detecting an event 514 on the monitor device 104 such as one of the event types 516 described above. For example, operation 602 can include detecting alarm triggered, alarm paused, alarm reset, alarm adjusted, alarm settings viewed, physiological variable trends viewed, patient information viewed, nuisance button 148 selected, and the like.

Next, the method 600 includes an operation 604 of generating a device usage log 500 in response to detection of the event 514 in operation 602. The device usage log 500 can be generated in accordance with the example shown in FIG. 5, and as described above.

Next, the method 600 includes an operation 606 of aggregating the device usage logs 500 generated from the monitor device 104 over a period of time. For example, the device usage logs 500 can be aggregated over a period of time such as 24 hours, one week, one month, or other period of time. In some examples, operation 606 can include aggregating the device usage logs 500 generated from the monitor device 104 with the device usage logs 500 generated by other monitor devices in the same healthcare facility, and/or in different healthcare facilities.

Next, the method 600 includes an operation 608 of determining key performance indicators (KPIs) based on device usage logs 500 that are uploaded and processed periodically. The KPIs determined in operation 608 can include any of the examples listed in Table 1, as well as additional types of KPIs. For example, operation 608 can include determining KPIs such as frequency of alarm setting changes and user interaction duration. The KPIs can include counts, and summary stats (e.g., percentages, and the like). All available metadata is counted to provide information about each feature of the monitor device 104 in various situations. In some examples, the KPIs can be processed into a "label" or "input" for complex model development.

Next, the method 600 includes an operation 610 of recommending an optimal alarm setting, an optimal user interface (UI) design, and/or an optimal user experience (UX) design for the monitor device 104 based on the KPIs determined in operation 608. The optimal alarm setting can be specialized based on the clinical environment of the monitor device 104 such as acuity level, hospital unit or department, nurse to patient ratio, and the like. Also, the optimal alarm setting can be specialized based on patient cohort or population. The optimal alarm setting can reduce alarm fatigue such as by reducing the need to manually change an alarm setting due to nuisance alarms, and thereby reducing user interactions with the monitor device.

The optimal alarm setting can be recommended in operation 610 for multiple monitor devices in the same unit or department of a healthcare facility, and for multiple monitor devices that monitor patients within the same patient cohort or population. Additionally, the optimal alarm setting can be recommended in operation 610 for multiple monitor devices across different healthcare facilities that have similar clinical environments and patient populations.

Figure 7:
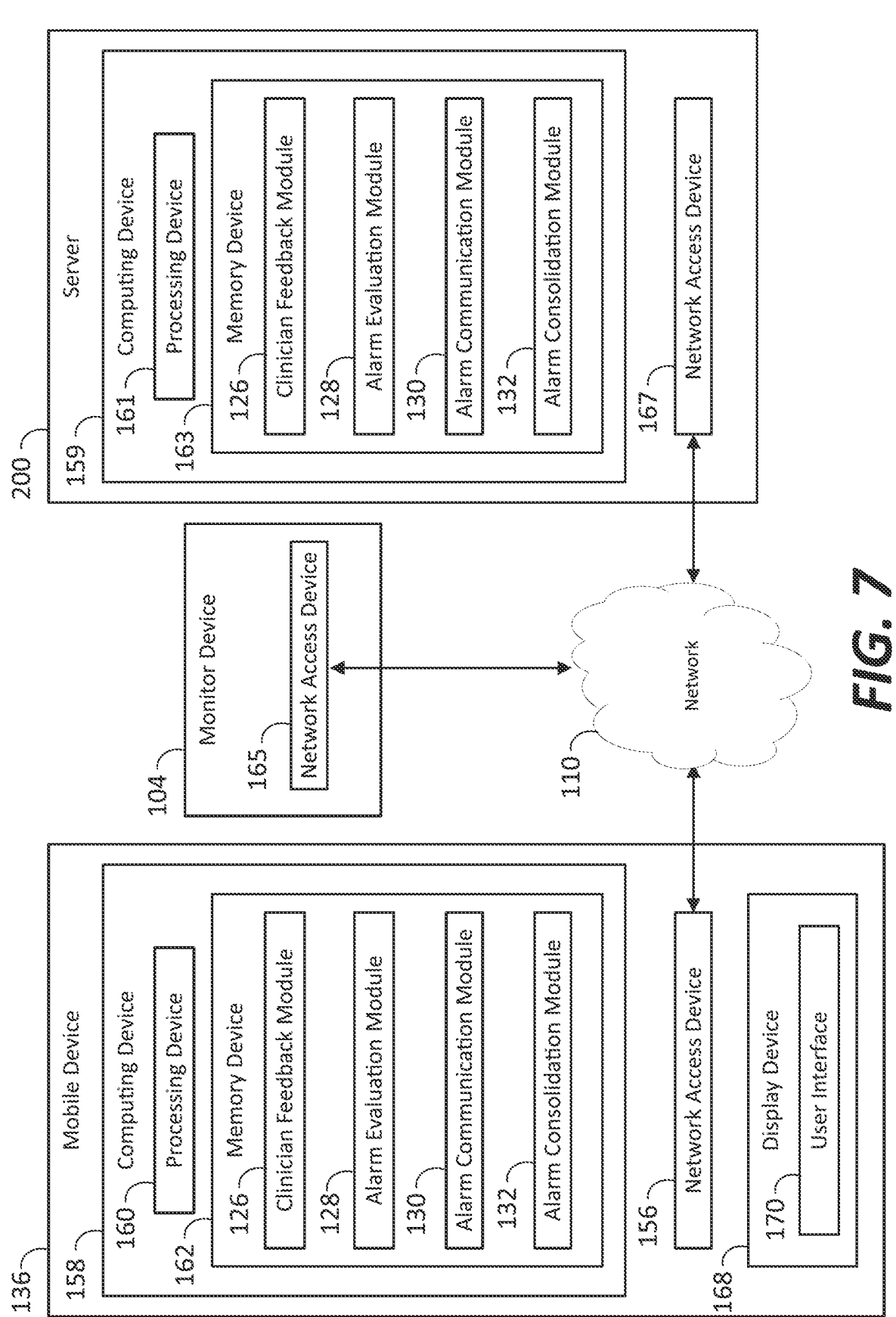
FIG. 7 schematically illustrates an example of the system of FIG. 1, which includes a mobile device in communication with the monitor device.

FIG. 7 schematically illustrates an example of the system 100 with the mobile device 136 in communication with the monitor device 104 and the server 200 via the communications network 110. In this example, the system 100 is a distributed alarm system in which data is collected by the monitor device 104 from various source devices such as the patient support system 102, the motion sensor 106, and the one or more physiological sensors 108, and alarm notifications are generated based on the collected data for distribution between the monitor device 104, the mobile device 136, and the server 200 via the communications network 110.

The mobile device 136 can be carried by a clinician around the healthcare facility while the clinician is caring for multiple patients admitted to the healthcare facility. The mobile device 136 can include a smartphone, a tablet computer, and other portable computing devices.

As shown in FIG. 7, the mobile device 136 includes a network access device 156 that operates to communicate with other devices over one or more networks, such as the communications network 110. Examples of the network access device 156 include wired network interfaces and wireless network interfaces. The mobile device 136 can communicate bidirectionally with the monitor device 104 and the server 200 through the communications network 110. In the example shown in FIG. 7, the monitor device 104 and the server 200 include network access devices 165, 167, respectively.

As further shown in FIG. 7, the mobile device 136 further includes a computing device 158 containing a processing device 160 and a memory device 162, and a display device 168, which operates to display a user interface 170. Other embodiments may include additional, different, or fewer components. The computing device 158, the processing device 160, the memory device 162, and the display device 168 of the mobile device 136 may be similar to the computing device 120, the processing device 122, the memory device 124, and the display device 114, respectively, of the monitor device 104 which have each been previously described.

As further shown in FIG. 7, the server 200 is also connected to the communications network 110, and includes a computing device 159 containing a processing device 161 and a memory device 163. Other embodiments may include additional, different, or fewer components. The computing device 159, the processing device 161, and the memory device 163 of the server 200 may be similar to the computing device 120, the processing device 122, the memory device 124, and the display device 114, respectively, of the monitor device 104 previously described.

As further shown in FIG. 7, the memory devices 162, 163 of the mobile device 136 and server 200 can each include the clinician feedback module 126, the alarm evaluation module 128, the alarm communication module 130, and the alarm consolidation module 132. The alarm communication module 130 and the alarm consolidation module 132 can work together to communicate alarm notifications between the monitor device 104, the mobile device 136, and the server 200 in a more efficient and intuitive manner to mitigate alarm fatigue.

The alarm communication module 130 operates to control communication of alarm notifications received by a clinician to reduce a total number of alarm notifications received by the clinician, and thereby mitigate alarm fatigue in a clinician environment such as a healthcare facility. For example, the alarm communication module 130 can control the communication of alarm notifications sent from the monitor device 104 and received by the mobile device 136.

The alarm communication module 130 controls communication of the alarm notifications by classifying alarms into groups based on severity levels. The alarm communication module 130 uses the severity levels to determine whether to push an alarm notification to the mobile device 136 or to allow the mobile device 136 to pull the alarm notification from the monitor device 104. Thus, the alarm communication module 130 allows for both push and pull alarm notifications. In this manner, the alarm communication module 130 can reduce the number of alarms received on the mobile device 136 to reduce alarm fatigue, while allowing valuable information to remain accessible by the clinician.

The alarm consolidation module 132 can ensure that information is presented to the clinician in an efficient and intuitive manner. For example, the alarm consolidation module 132 can prioritize alarms in an efficient manner for the clinician to act on. The alarm consolidation module 132 can help a clinician view and interpret alarm notifications by sorting the alarm notifications based on urgency using clinical data not readily available for viewing.

Figure 8:
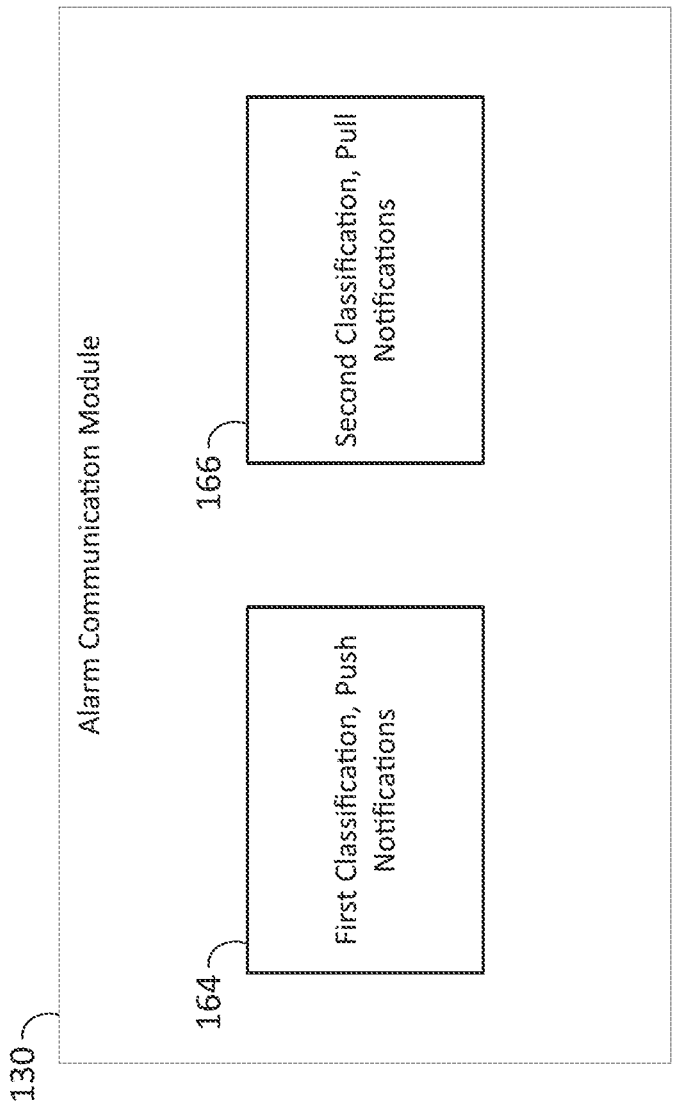
FIG. 8 schematically illustrates an example of an alarm communication module installed on the mobile device of FIG. 7.

FIG. 8 schematically illustrates an example of the alarm communication module 130 which provides different groups for classifying alarm communications based on alarm severity. The alarm communication module 130 includes a first group 164 in which alarm notifications are pushed to the mobile device 136, and a second group 166 in which alarm notifications are aggregated until a predefined condition is met. When the predefined condition is met, the alarm notifications are converted into the first group 164 and are pushed to the mobile device 136.

Otherwise, when the predefined condition is not met, the aggregated alarm notifications can be pulled by the mobile device 136 for viewing by the clinician. In this manner, alarm notifications in the first group 164 are communicated to the clinician, while alarm notifications in the second group 166 are accessible by the clinician. Advantageously, this can reduce the total number of alarm notifications communicated to the clinician, while allowing the clinician to have access on the mobile device 136 to all alarm notifications.

The alarm communication module 130 is configurable on the monitor device 104 or on the mobile device 136 to determine which alarm severity levels are pushed to the mobile device 136, and which ones are not. In one example, the alarm communication module 130 is configurable such that only high severity alarm notifications are pushed to the mobile device 136, while moderate and low severity alarm notifications can be pulled by the mobile device 136. In another example, the alarm communication module 130 is configurable such that both high severity and moderate severity alarm notifications are pushed to the mobile device 136, while low severity alarm notifications can be pulled by the mobile device 136.

In further examples, the alarm communication module 130 is configurable on the monitor device 104 or on the mobile device 136 to allow a user to decide which alarm notifications are considered high severity, moderate severity, and low severity. The severity levels can be based on urgency of intervention. For example, the urgency of intervention can be based on an estimated or predicted onset of patient harm such as immediate, prompt, or delayed. Also, the severity levels can be based on types of resources required for an intervention.

In some examples, access to configure the alarm communication module 130 is granted only to an administrator or person having designated credentials in the healthcare facility where the monitor device 104 and mobile device 136 are deployed. In other examples, the monitor device 104 or the mobile device 136 grant access to a clinician for configuring the alarm communication module 130 such by requesting the clinician to enter their badge ID into the monitor device 104. When granted access, the clinician can select the settings tab 154e displayed on the monitor device 104 (see FIG. 3) to display a settings screen to adjust or reconfigure the alarm communication module 130. Additionally, or as an alternative, the clinician can adjust or reconfigure the alarm communication module 130 on the mobile device 136.

Figure 9:
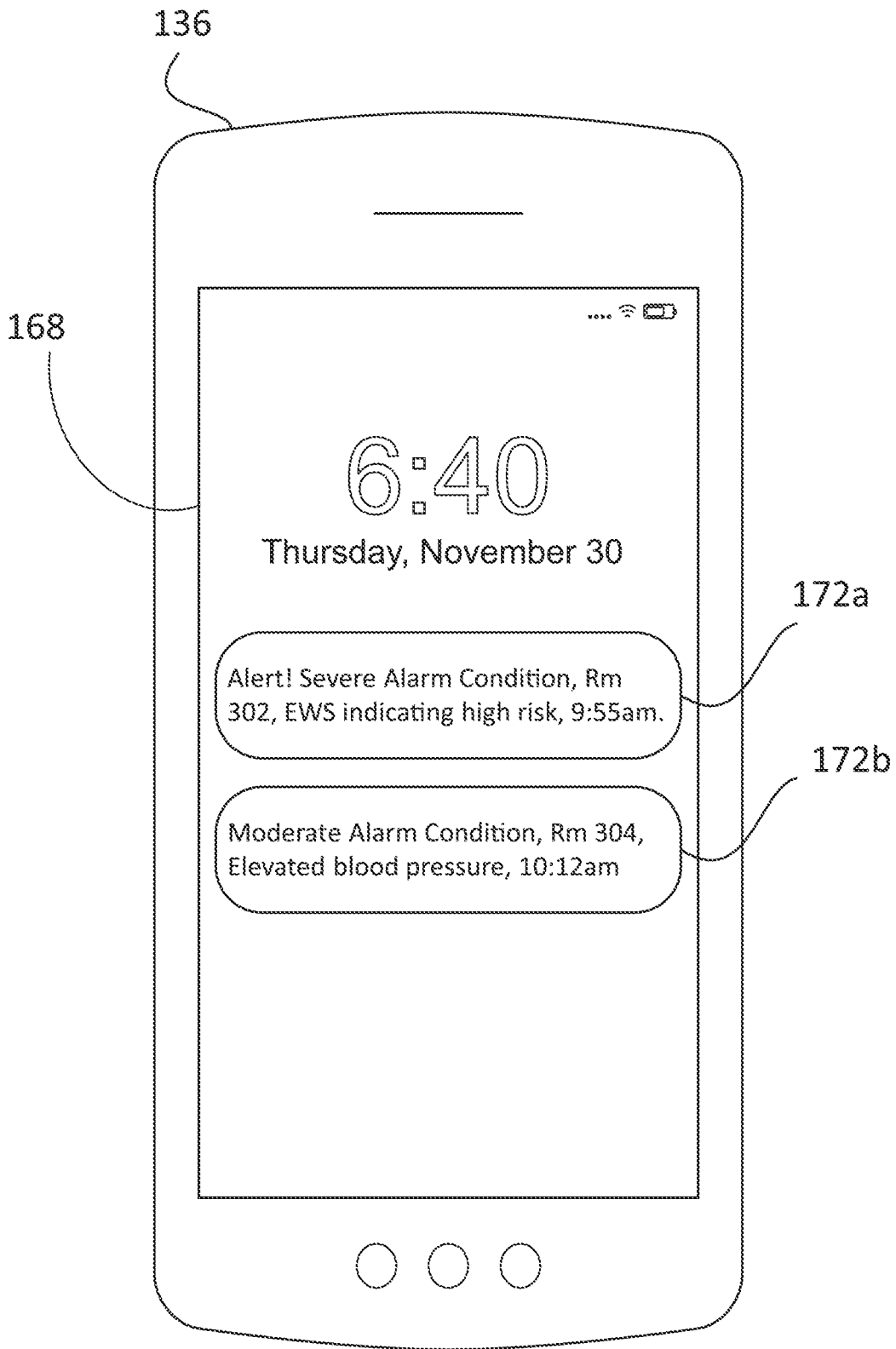
FIG. 9 illustrates an example of alarm notifications that are displayed on the mobile device of FIG. 7 for alerting a clinician.

FIG. 9 illustrates an example of alarm notifications that can be displayed on the mobile device 136 in accordance with the first group 164 of alarm notifications defined in the alarm communication module 130. Alarm notifications that are classified in accordance with the second group 166 of alarm notifications defined in the alarm communication module 130 are not displayed on the mobile device 136 to mitigate alarm fatigue.

In the example shown in FIG. 9, first and second alarm notifications 172a, 172b are displayed on a lock screen of the mobile device 136. In addition, or alternatively, the first and second alarm notifications 172a, 172b can be displayed on a notification center of the mobile device 136. While two alarm notifications are shown displayed on the mobile device 136, more than two alarm notifications, or fewer than two alarm notifications can be displayed.

The first alarm notification 172a can include a first component such as a message identifying the alarm notification (e.g., "Alert! Severe Alarm Condition"), a second component identifying a location from where the alarm notification originated (e.g., room 302), a third component identifying a principle cause for the alarm notification (e.g., early warning score indicating high risk), and a fourth component such as a time stamp (e.g., 9:55 am). Similarly, the second alarm notification 172b can include a first component (e.g., "Moderate Alarm Condition"), a second component (e.g., room 304), a third component (e.g., elevated blood pressure), and a fourth component (e.g., 10:12 am). Alternative configurations for the alarm notifications are possible such that the alarm notifications may include additional components to display additional information, or may includer fewer components to display less information.

The clinician can tap or swipe each alarm notification to delete or ignore the alarm notifications. Also, the clinician can unlock the lock screen of the mobile device 136 to obtain access to additional information on the alarm notifications and patient condition. For example, the clinician can unlock the lock screen of the mobile device 136 to pull alarm notifications classified under the second group 166 defined in the alarm communication module 130.

In some examples, the alarm notifications are ranked in chronological order on the mobile device 136 such that earlier alarm notifications (e.g., the first alarm notification 172a received at 9:55 am) are displayed above later alarm notifications (e.g., the second alarm notification 172b received at 10:12 am). Alternatively, the alarm notifications can be ranked based on severity such that severe alarm notifications (e.g., the first alarm notification 172a which is a severe alarm condition) are ranked above less severe alarm notifications (e.g., the second alarm notification 172b which is a moderate alarm condition). In some examples, the alarm notifications ranking is dynamically updated as new alarm notifications are received.

Figure 10:
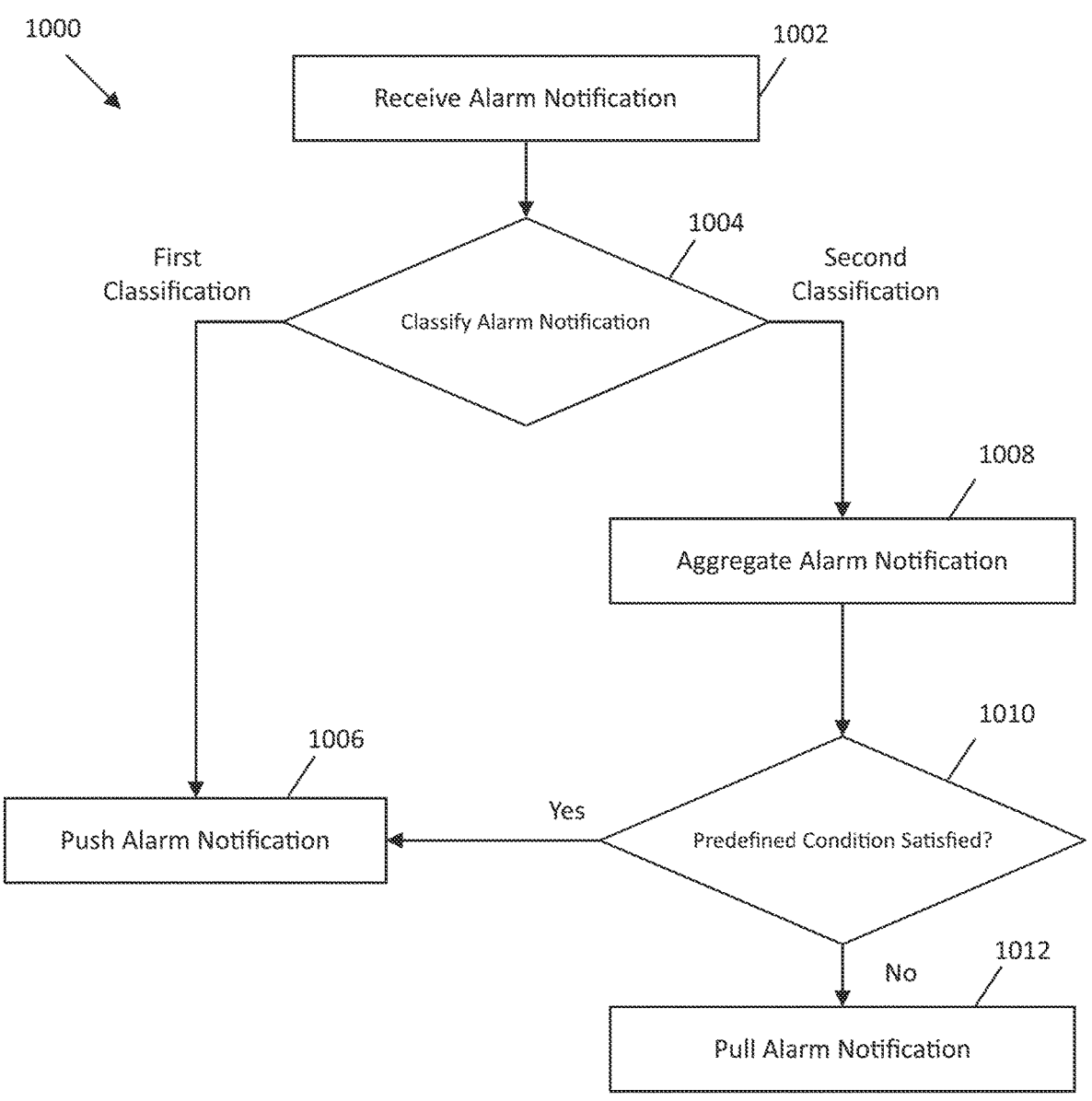
FIG. 10 schematically illustrates an example of a method of communicating alarm notifications to the mobile device of FIG. 7.

FIG. 10 schematically illustrates an example of a method 1000 of communicating alarm notifications to the mobile device 136. In some instances, the alarm notifications are communicated directly from the monitor device 104 to the mobile device 136. In alternative examples, the alarm notifications can be communicated from the server 200 to the mobile device 136. In some examples, the method 1000 is performed by the alarm communication module 130.

As shown in FIG. 10, the method 1000 includes an operation 1002 of receiving a notification that an alarm is triggered by one or more of the physiological variables monitored by one or more of the source devices (e.g., the patient support system 102, the motion sensor 106, and the physiological sensors 108) connected to the monitor device 104. In some examples, the alarm is triggered by an early warning score (EWS) exceeding a threshold value, where an early warning score is a composite score based on multiple physiological parameters (e.g., respiratory rate, oxygen saturation, temperature, blood pressure, pulse/heart rate, AVPU response).

Next, the method 1000 includes an operation 1004 of classifying the alarm notification received in operation 1002. Operation 1004 can include classifying the alarm notification under the first group 164, in which case the method 1000 proceeds to an operation 1006 of pushing the alarm notification to the mobile device 136 of a clinician.

Operation 1004 can also include classifying the alarm notification under the second group 166, in which case the method 1000 proceeds to an operation 1008 of aggregating the alarm notification with other alarm notifications for the patient.

Next, the method 1000 includes an operation 1010 of determining whether a predefined condition is satisfied. The predefined condition can be based on a combination of alarm notifications that when considered in combination indicate a high severity level, despite the alarm notifications when considered individually do not have a high severity level.

As an illustrative example, an alarm from an SpO2 sensor is triggered because a signal from the sensor is no longer detected. This type of alarm may be classified as having a low severity level because it is likely that the SpO2 sensor fell of the patient's finger. However, when an alarm from an end tidal carbon dioxide (etCO2) sensor is also triggered, the combination of the SpO2 and etCO2 sensors being triggered can indicate that there is a high severity level. In such a case, a predefined condition is determined as satisfied in operation 1010, and the method 1000 proceeds to the operation 1006 of pushing the alarm notification to the mobile device 136.

As another illustrative example, a predefined condition can be based on whether a certain number of events have happened within a predetermined period of time. For example, if an alarm of a respiration rate sensor is triggered more than 5 times within a 30 minute period of time, this can indicate a high severity level such that a predefined condition is determined as satisfied in operation 1010, and the method 1000 proceeds to the operation 1006.

When a predefined condition is not determined in operation 1010 as being satisfied, the method 1000 proceeds to an operation 1012 of providing the alarm notification as a pull notification that can be pulled from the mobile device 136. In accordance with the method 1000, a clinician is provided access to all alarm notifications (e.g., by providing pull notifications), however, only alarm notifications that are determined as having a high severity level or that satisfy a predefined condition are pushed to the mobile device 136.

In this manner, alarms that are for delayed onset of patient deterioration that are not clinically actionable are not automatically pushed to the mobile device 136. Instead, these alarms are consolidated and/or aggregated with other alarms until they reach a point where an intervention by the clinician is required (e.g., when the predefined condition is satisfied).

Additionally, the consolidated and/or aggregated alarm notifications can be summarized at the end of the clinician's shift or when there is a need to communicate a patient condition to another clinician. In this manner, the consolidated and/or aggregated alarm notifications can help hand-offs between clinicians in the healthcare facility.

Figure 11:
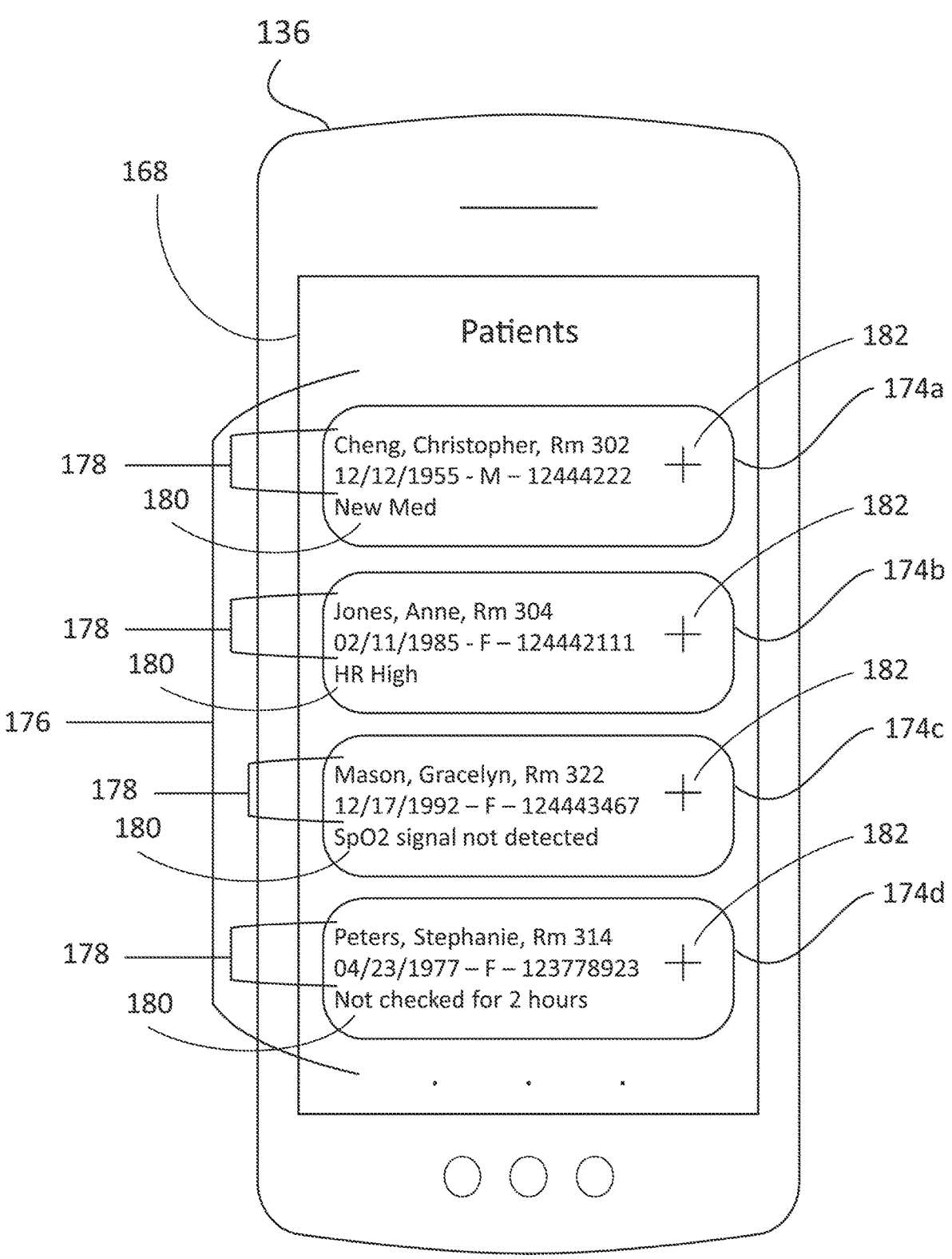
FIG. 11 illustrates an example of alarm notifications that are consolidated by patient and ranked by urgency for display on the mobile device of FIG. 7.

FIG. 11 illustrates an example of alarm notifications 174a-174d that are consolidated by patient and ranked by urgency for display on the mobile device 136. As described above, the system 100 can be a distributed alarm system in which data is collected by the monitor device 104 from various source devices that are configured based on care environment and workflow such as the patient support system 102, the motion sensor 106, and the one or more physiological sensors 108. The alarm notifications 174a-74d are generated based on the collected data.

In some examples, the monitor device 104 generates the alarm notifications 174a-174d based on the collected data from the source devices, and sends the alarm notifications 174a-174d to the mobile device 136 via the communications network 110. Alternatively, the monitor device 104 can forward data collected from the source devices to the server 200, and the server 200 generates and sends the alarm notifications 174a-174d to the mobile device 136 via the communications network 110.

In FIG. 11, the alarm notifications 174a-174d displayed on the mobile device 136 are examples of priority queue groups that consolidate alarms per patient. In other examples, alarm notifications can include priority queue groups that consolidate alarms per type of alarm event, type of resource required for an intervention (e.g., personnel, equipment, medications, etc.), and other types of attributes that can be used to consolidate alarms in the healthcare facility.

The alarm consolidation module 132 ranks the alarm notifications 174a-174d by severity in a priority queue 176 where the first ranked alarm notification (e.g., the alarm notifications 174a) has the highest priority, a subsequently ranked alarm notification (e.g., the alarm notifications 174b) has the next highest priority, and so on. The alarm consolidation module 132 can include a ranking algorithm to determine an order of the alarm notifications in the priority queue 176. The ranking algorithm can dynamically update the order of the alarm notifications in the priority queue 176 as new data is collected from the source devices.

In the example shown in FIG. 11 in which the alarm notifications 174a-174d consolidate alarms per patient, the ranking algorithm can use any combination of factors to determine the order of the priority queue 176 such as, without limitation, patient risk level, patient treatment markers, types of active alarms for the patient, duration of active alarms for the patient, magnitude of violation by active alarms, time since the patient was last checked, and source device from which the active alarms are triggered and/or potential artifacts are detected (e.g., the patient support system 102, the motion sensor 106, the one or more physiological sensors 108, an infusion pump, a ventilator, and the like). In examples in which the alarm notifications 174a-174d consolidate alarms according to a different type of attribute, different factors and combinations thereof may be used to determine the order of the priority queue 176.

The alarm notifications 174a-174d each display information that identifies a particular patient, and a most significant factor or a primary cause for the ranking of the alarm notification in the priority queue 176. For example, each of the alarm notifications 174a-174d includes a first component 178 that displays information identifying the patient such as the patient's name, room number (or location within the healthcare facility), date of birth, sex, and medical record number. In other examples, additional, different, or less information for identifying the patient can be included in the alarm notifications 174a-174d.

Each of the alarm notifications 174a-174d further includes a second component 180 that identifies the most significant active alarm and/or patient condition on which the ranking of the alarm notification 174a-174d in the priority queue 176 is based. In the example illustrated in FIG. 11, the second component 180 for the alarm notification 174a is "New Med" (e.g., a new medication with potential side effects has been administer to the patient), the second component 180 for the alarm notification 174b is "HR High" (e.g., measured heart rate exceeds an upper limit of a heart rate alarm), the second component 180 for the alarm notification 174c is "SpO2 signal not detected" (e.g., possibly due to a pulse oximeter sensor having become detached from the patient), and the second component 180 for the alarm notification 174d is "Not checked for 2 hours" (e.g., the patient has not been checked on by a clinician for more than two hours).

A clinician can select or touch an alarm notification 174a-174d that is displayed on the display device 168 (e.g., using their finger in examples where the display device 168 is a touchscreen) to expand a list of consolidated active alarms and/or patient conditions for the alarm notification. As an illustrative example, each of the alarm notifications 174a-174d can include a third component 182 that can be selected by a clinician to expand and contract a list of consolidated active alarms and/or patient conditions. In the illustrative example provided in FIG. 11, each third component 182 is displayed as a plus sign "+" that can be selected to expand a list of consolidated active alarms and/or patient conditions for each of the alarm notifications 174a-174d in the priority queue 176 displayed on the mobile device 136.

Figure 12:
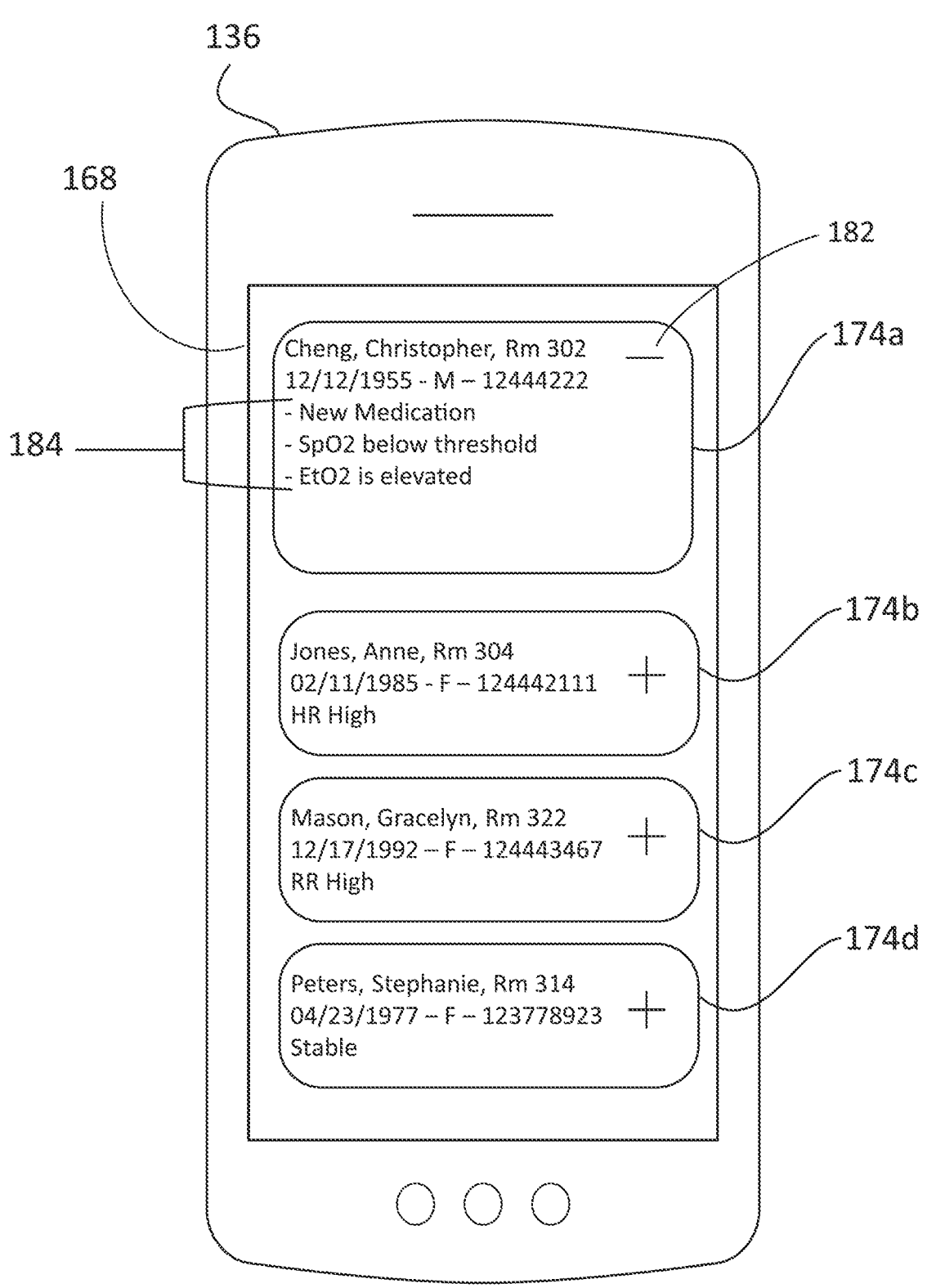
FIG. 12 illustrates an example of an alarm notification from FIG. 11 displayed in an expanded view showing active alarms for a patient displayed in a consolidated list.

FIG. 12 illustrates an example of the priority queue 176 from FIG. 11 with the alarm notification 174a displayed in an expanded view in response to a selection of the alarm notification 174a. In this example, the third component 182 is converted into a minus sign "−" such that the third components 182 can be selected to contract the list of consolidated active alarms and patient conditions in the alarm notification 174a. In alternative examples, the clinician can simply select or touch the alarm notification 174a for a second time to contract the list of consolidated active alarms and/or patient conditions for the alarm notification 174a.

When in the expanded view, the alarm notification 174a displays a consolidated list 184 of active alarms and patient conditions that led to the alarm notification 174a being pushed to the mobile device 136. The active alarms and patient conditions are sorted by priority rank in the consolidated list 184. For example, "new medication" is ranked first because this is the most significant factor or the primary cause for the ranking of the alarm notification 174a, as identified by the second component 180 of the alarm notification 174a shown in FIG. 11.

In the illustrative example shown in FIG. 12, additional active alarms and patient conditions in the consolidated list 184 include "SpO2 below threshold" and "EtO2 is elevated". These active alarms were not displayed by the second component 180 of the alarm notification 174a shown in FIG. 11 because these active alarms may be secondary or ancillary factors that led to the alarm notification 174a being pushed to the mobile device 136.

In this manner, the alarm communication module 130 and the alarm consolidation module 132 can work together to push the alarm notifications 174 to the mobile device 136 of a clinician where the most significant active alarm and/or patient condition is displayed on the alarm notifications 174, and secondary or ancillary active alarms and patient conditions are displayed by expanding each alarm notification 174a to display the consolidated list 184.

In some examples, the alarm consolidation module 132 does not suppress any of the alarms identified in the consolidated list 184. Instead, the alarm consolidation module 132 displays the active alarms in the priority rank. As the active alarms are being resolved, the alarm consolidation module 132 can dynamically update the consolidated list 184. Additionally, the alarm consolidation module 132 can dynamically update the consolidated list 184 to include new alarms that may surface or be triggered before an intervention by the clinician. Furthermore, the ranking of the alarm notifications in the priority queue 176 can be dynamically updated based on the new alarms that may surface or be triggered before an intervention by the clinician.

In some examples, the alarm consolidation module 132 can allow the clinician to remotely suppress the active alarms that are flashing or beeping on one or more of the source devices proximate to the patient to minimize alarm fatigue on the patient, while continuing to display the active alarms in the consolidated list 184 until they are resolved by the clinician.

Figure 13:
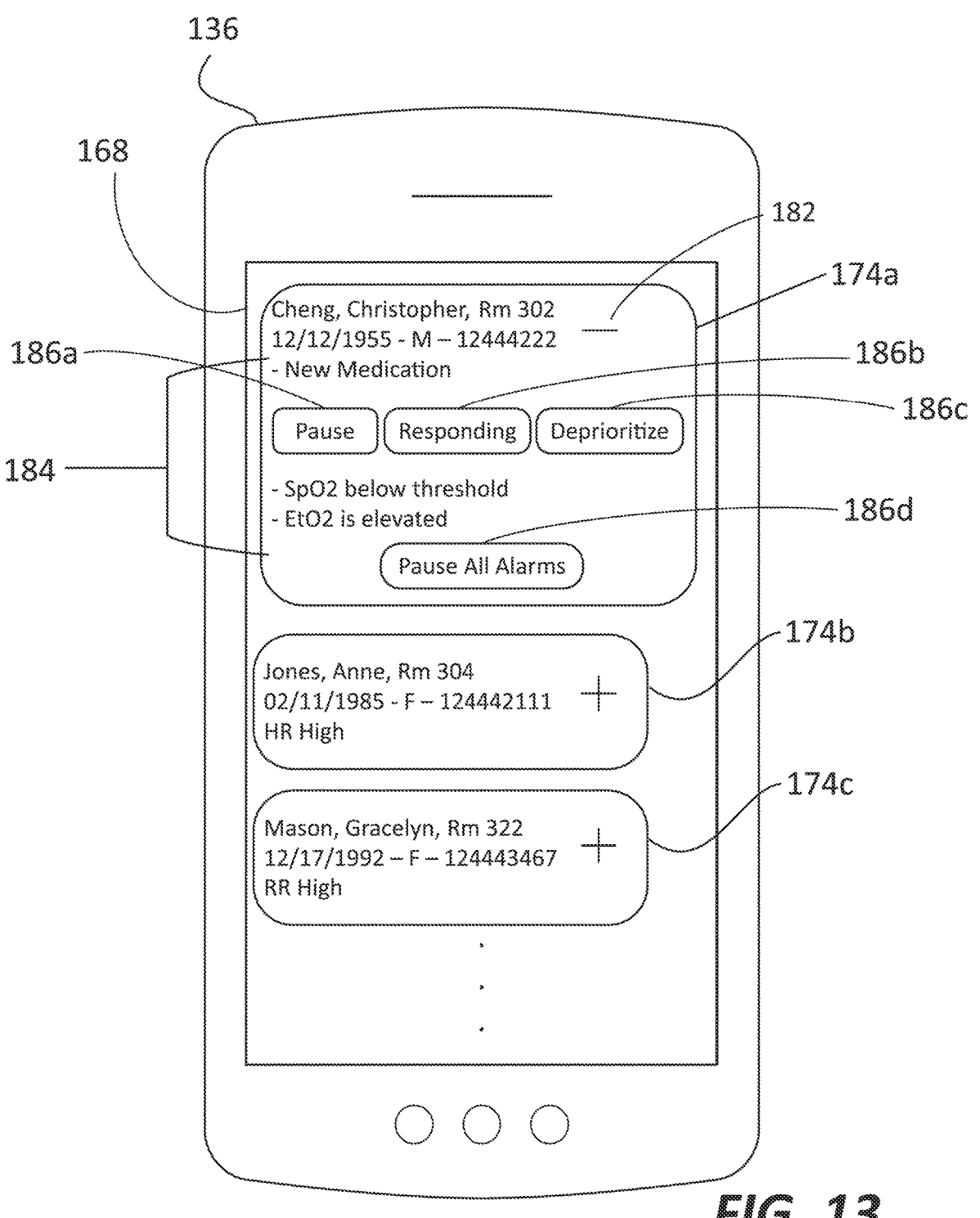
FIG. 13 illustrates an example of an alarm notification from FIG. 12 that includes feedback inputs that are selectable for an active alarm selected from the consolidated list.

FIG. 13 illustrates another example of the alarm notification 174a that includes feedback inputs 186a-186c for a clinician to select a response to an active alarm (e.g., "New Medication"). The feedback inputs 186a-186c can be displayed in response to a selection of an active alarm from the consolidated list 184. In this example, the feedback inputs 186a-186c include a feedback input 186a to pause the active alarm, a feedback input 186b to indicate that the clinician is responding to the active alarm, and a feedback input 186c to deprioritize the active alarm. Also, a feedback input 186d can be provided to pause all active alarms in the consolidated list 184 of the alarm notification 174a for a predetermined period of time.

In some examples, the alarm evaluation module 128 can receive clinician feedback from the feedback inputs 186a-186d to improve alarm algorithms that are used to generate the alarm notifications 174. For example, the alarm evaluation module 128 can improve the alarm algorithms based on a device usage log similar to the one shown in FIG. 5, and described above.

As an illustrative example, the alarm evaluation module 128 can keep track of alarm metrics for continuous improvement of both the ranking of the alarm notifications 174 in the priority queue 176, as well as the ranking of the active alarms and patient conditions that are included in the consolidated list 184 of each alarm notification 174. For example, the alarm evaluation module 128 can monitor de-prioritization rate, response rate, and pause rate by monitoring usage of the feedback inputs 186a-186d that are selected for the active alarms and patient conditions included in the consolidated lists 184 for each of the alarm notifications 174.

Additional examples of alarm metrics that can be monitored by the alarm evaluation module 128 to improve alarm algorithms can include average prioritization ranking of each active alarm and patient condition, biggest contributors to alarm flooding situations (e.g., when an excessive number of alarms occur within a short period of time), events that follow alarm flooding situations, sets of active alarms and/or patient conditions that are often ranked together. Additional alarm metrics that can be monitored to improve alarm algorithms are contemplated.

The alarm metrics can be used to improve alarm algorithms through hybrid approaches of machine learning and human auditing. In one example, a model that is highly human interpretable, such as a decision tree, is used. In this example, human auditors can audit the tree structure to determine ways to improve alarm algorithms and rankings of the alarm notifications and underlying active alarms based on care environment and workflow.

In another example, a model that is not human interpretable can be used. In such example, regular audits of the active alarm and patient condition rankings are performed, and the results of the audits are used to re-train the model to improve alarm algorithms and rankings of the alarm notifications and underlying active alarms based on care environment and workflow.

The various embodiments described above are provided by way of illustration only and should not be construed to be limiting in any way. Various modifications can be made to the embodiments described above without departing from the true spirit and scope of the disclosure.

What is claimed is:

1. A device for monitoring a patient, comprising:
a display device;
at least one processing device; and
a memory device storing instructions which, when executed by the at least one processing device, cause the device to:
   display a status area on the display device that includes an alarm pause input and a nuisance button separate from the alarm pause input, wherein the alarm pause input is selectable to pause an active alarm for a predetermined interval;
   receive clinician feedback from a selection of the nuisance button or a selection of the alarm pause input;
   pause the active alarm in response to the clinician feedback from the selection of the nuisance button or the selection of the alarm pause input;
   identify one or more alarm settings responsible for the clinician feedback received via the selection of the nuisance button; and
   adjust the one or more alarm settings based on the clinician feedback.

2. The device of claim 1, wherein the status area further displays a message regarding a status of the patient being monitored by the device.

3. The device of claim 1, wherein the one or more alarm settings are adjusted based on a learning rate that determines a speed for adjusting the one or more alarm settings.

4. The device of claim 3, wherein the speed of the learning rate is based on time duration or a threshold number of selections of the nuisance button.

5. The device of claim 3, wherein the speed of the learning rate is adjustable.

6. The device of claim 1, wherein the clinician feedback is recorded in a device usage log for monitoring usage of the nuisance button.

7. The device of claim 6, wherein the device usage log is a clickstream data schema that is generated each time the nuisance button is selected.

8. The device of claim 6, wherein the device usage log is aggregated with additional device usage logs to recommend optimal alarm settings based on key performance indicators.

9. The device of claim 1, wherein an alarm notification is generated based on the active alarm, and wherein the alarm notification is classified into a first group in which the alarm notification is a push notification, or a second group in which the alarm notification is a pull notification.

10. The device of claim 9, wherein the alarm notification is pushed to a mobile device, and wherein the alarm notification includes at least a first component identifying the patient and a second component identifying a most significant active alarm or patient condition.

11. The device of claim 9, wherein the alarm notification is configured to display a consolidated list of active alarms and patient conditions sorted by priority rank.

\* \* \* \* \*